United States Patent [19]

Joji et al.

[11] 4,304,937

[45] Dec. 8, 1981

[54] PROCESS OF PREPARING CARBOXYLIC ACID AMIDES

[75] Inventors: Nishikido Joji, Fuji; Tamura Nobuhiro, Tokyo; Fukuoka Yohei, Kurashiki, all of Japan

[73] Assignee: Asahi Kasei Kogyo Kabushiki Kaisha, Osaka, Japan

[21] Appl. No.: 93,370

[22] Filed: Nov. 13, 1979

[30] Foreign Application Priority Data

Nov. 17, 1978 [JP] Japan .................................. 53-141216

[51] Int. Cl.$^3$ ............................................ C07C 102/00
[52] U.S. Cl. ...................................... 564/204; 542/414; 542/424; 542/425; 546/224; 546/315; 546/316; 546/317; 260/239.1; 260/326.2; 260/347.3; 549/70; 564/123; 564/161; 564/215; 544/16; 544/25; 544/367; 544/372; 544/379; 544/382; 548/373; 548/379
[58] Field of Search ............. 260/561 R, 347.3, 326.2, 260/347.2; 546/314, 315, 316, 317; 564/204, 215, 123, 161; 549/70

[56] References Cited

FOREIGN PATENT DOCUMENTS 2422887 11/1975 Fed. Rep. of Germany ... 260/561 R

OTHER PUBLICATIONS

Kendall, General Chemistry, Revised Ed., pp. 22-23, 304 to 306, D. Appleton-Century Co., NY (1936).
Nakagawa et al., Chem. Abstracts, vol. 64, col. 8075 (1966) (abst. of Chem. Commun. 1966 (1), 17-18).
Nakagawa et al., Chem. Commun. 1966 (1), 17-18.

*Primary Examiner*—John D. Randolph
*Attorney, Agent, or Firm*—Sprung, Felfe, Horn, Lynch & Kramer

[57] ABSTRACT

A process of preparing a carboxylic acid amide which comprises reacting (a) an aldehyde with (b) at least one compound selected from the group consisting of ammonia, a primary amine and a secondary amine in the presence of a molecular oxygen-containing gas and palladium metal or platinum metal as the catalyst.

10 Claims, No Drawings

PROCESS OF PREPARING CARBOXYLIC ACID AMIDES

DESCRIPTION OF THE PRIOR ART

It is known that carboxylic acid amides as industrially useful substances can be prepared by the reaction between carboxylic acids or their esters and amines or by the hydrolysis of the corresponding nitriles. Although the yield by these processes is at an almost satisfactory level due to the recent technical advances, the preparation of carboxylic acid amides require several steps starting from petrochemical raw materials. For example, according to British Pat. No. 925,588, N,N-dimethylformamide is prepared by reacting carbon monoxide with dimethylamine in order to shorten its preparation steps. However, this process requires high presures and complicated operations for treating by-products including formic acid. Thus, development of a simpler and more economic process from an industrial viewpoint has been expected.

BACKGROUND OF THE INVENTION

Field of the Invention

This invention relates to a process of preparing carboxylic acid amides. More particularly, it relates to a process of preparing carboxylic acid amides by reacting an aldehyde with ammonia or an amine in the presence of a molecular oxygen-containing gas using a catalyst.

SUMMARY OF THE INVENTION

According to this invention there is provided a process of preparing a carboxylic acid amide which comprises reacting (a) an aldehyde with (b) at least one compound selected from the group consisting of ammonia, a primary amine and a secondary amine in the presence of a molecular oxygen-containing gas and palladium metal or platinum metal.

DETAILED DESCRIPTION OF THE INVENTION

The aldehydes (1) which can be employed as one of the starting materials in this invention include saturated aliphatic aldehydes such as formaldehyde, acetaldehyde, propionaldehyde, pivalinaldehyde and caprylaldehyde; unsaturated aliphatic aldehydes such as acrolein and methacrolein; aromatic aldehydes such as benzaldehyde, tolualdehyde and cinnamaldehyde, the aromatic aldehydes whose aromatic ring is substituted with a halogen atom such as chlorine, bromine and fluorine; an alkyl group having 1 to 5 carbon atoms such as methyl, ethyl, propyl or n-amyl; a haloalkyl group having 1 to 5 carbon atoms such as chloromethyl and bromoethyl; or an alkoxy group such as methoxy and ethoxy; heterocyclic aldehydes such as furfural, pyridinealdehyde, thiophenealdehyde and pyrrolealdehyde; the heterocyclic aldehydes whose heterocyclic ring is substituted with an alkyl group having 1 to 5 carbon atoms such as methyl, ethyl, isopropyl, n-amyl; a haloalkyl group having 1 to 5 carbon atoms such as chloromethyl and bromoethyl; and polyaldehydes such as glyoxal and glutardialdehyde.

Of these aldehydes, formaldehyde, the aldehydes in which the carbon atom in the α-position does not have a hydrogen atom such as benzaldehyde, the substituted benzaldehydes, pyridinealdehyde, the substituted furfurals and the aldehydes in which the carbon atom in the α-position has an unsaturated double bond such as acrolein and methacrolein are preferred due to their excellent reactivity in the process of this invention. More preferred aldehydes are formaldehyde, pyridinealdehyde such as picolinealdehyde, nicotinealdehyde and isonicotinealdehyde, and furfural.

The other starting material of this invention is (b) ammonia, a primary amine or a secondary amine.

Exemplary primary amines which can be employed in this invention include aliphatic primary amines such as methylamine, ethylamine, propylamine, isopropylamine and butylamine; alicyclic primary amines such as cyclopentylamine and cyclohexylamine; aromatic primary amine such as aniline, toludine and naphthylamine; aromatic alkyl primary amine such as benzylamine and xylidenediamine; and primary amines having a penicillin skeleton or a cephalosporin skeleton. Further, any other primary amines can be employed in this invention.

Exemplary secondary amines which can be employed in this invention include aliphatic secondary amines such as dimethylamine, diethylamine, di-n-propylamine and methylethylamine; aromatic secondary amines such as methylaniline and ethylaniline; and nitrogen-containing heterocyclic compounds in which the nitrogen atom in the heterocyclic ring forms a secondary amine such as piperidine, piperazine, pyrazoline, pyrrolidine and pyrroline.

Also, the above described primary and secondary amines may have a substituent such as a halogen atom such as chlorine, bromine and fluorine; an alkyl group such as methyl, ethyl, isopropyl and n-octyl; or an alkoxy group such as methoxy and ethoxy, in the carbon atom which constitutes the amine compounds.

Of these compounds, preferred compounds are ammonia, the above described primary amines, dimethylamine, diethylamine, methylethylamine, piperidine and piperazine. More preferred compounds are ammonia, methylamine, ethylamine, dimethylamine and diethylamines.

The amount of the ammonia, the primary amine or the secondary amine employed in this invention can be varied depending upon the aldehyde selected but typically ranges from about 0.002 mole to about 100 moles per mole of the aldehyde. A preferred amount is at least about 0.01 mole per mole of the aldehyde.

The molecular oxygen-containing gas which can be employed in this invention may be either molecular oxygen gas as such or a mixed gas of molecular oxygen gas with a diluting gas which is inert to the reaction such as nitrogen or carbon dioxide, including air.

The amount of the molecular oxygen which is present in the reaction system of this invention is at least a stoichiometric amount required for the reaction and preferably at least an amount 1.5 times as much as the stoichiometric amount.

In conducting the reaction of this invention, palladium metal or platinum metal is employed as the catalyst. It is preferred that the palladium metal or the platinum metal is supported on a carrier. Any conventional carriers such as active carbon, silica or alumina may be employed. The amount of the palladium metal or platinum metal supported on a carrier typically ranges from about 0.1 to about 20 percent by weight based on the weight the carrier. A preferred amount of the palladium metal or the platinum metal is from about 0.5 to about 10 percent by weight based on the weight of the carrier.

Furthermore, in order to obtain much better results, the palladium metal or the platinum metal is incorporated with at least one metal atom selected from the group consisting of lead, thallium and mercury. Such metal atoms may be employed either in the form of the metal as such or as the compound containing the atom. Exemplary compounds containing the lead, thallium or mercury atom employed in this invention include the halides, the inorganic acid salts, the organic acid salts, the oxides and the hydroxides of lead, thallium or mercury. The halides include the chlorides, the bromides, the iodides the fluorides of lead, thallium or mercury; the inorganic acid salts include the sulfates, the nitrates, the phosphates and the borates of lead, thallium or mercury; and the organic acid salts include the formates, acetates, propionates, the stearates, the malonates, the succinates, the glutarates, maleates, the benzoates and the phthalates of lead, thallium or mercury.

The atomic ratio of lead, thallium or mercury to palladium or platinum which can be employed in this invention typically ranges from about 0.01 to about 30 and preferably from about 0.1 to about 10 per atom of palladium or platinum.

Any conventional methods may be employed in the preparation of the palladium or platinum metal catalyst of this invention. For example, in an aqueous solution of a palladium salt or a platinum salt was immersed a carrier. Then the palladium salt or the platinum salt supported adsorbed on the carrier is dried and subjected to reduction with hydrogen, hydrazine or formalin to form the palladium metal or the platinum metal.

Further, incorporation of at least one metal atom selected from the group consisting of lead, thallium and mercury with the palladium metal or the platinum metal may be conducted in any conventional methods. For example, a carrier is added to an aqueous solution of lead acetate and the mixture is stirred for several hours to adsorb the lead acetate on the carrier. The lead acetate adsorbed on the carrier is calcined at a temperature of from about 500° C. to about 700° C. and then is added to an aqueous solution of palladium chloride and the mixture obtained is stirred for several hours. The palladium chloride adsorbed on the lead acetate which had been supported on the carrier is subjected to reduction with hydrogen, formalin or hydrazine. When platinum metal is employed together with a lead salt, the platinum metal supported on a carrier is added to an aqueous solution of a lead salt and the mixture is stirred sufficiently and dried. When the lead, thallium or mercury atom is incorporated with the palladium metal or the platinum metal, it is preferred that a carrier for supporting the metal atom together with the palladium metal or the platinum metal is employed.

The amount of the palladium metal or the platinum metal supported on a carrier which can be employed in this invention typically ranges from about 0.1 to about 20 percent by weight and preferably from about 0.5 to about 10 percent by weight based on the weight of the carrier.

When the palladium metal is compared with the platinum metal in the catalytic efficiency, the palladium metal as such or in combination of the lead, thallium or mercury atom gives a better result than the platinum metal.

The reaction temperature which can be employed in this invention is typically from about 0° C. to about 200° C. A preferred temperature range is from about 15° C. to about 150° C. Thus, as one of the characteristic features of this invention, the reaction can be conducted at comparatively low temperatures, and even around room temperature the reaction of this invention has oxidative activity.

Further, in order to render the starting materials of this invention soluble, a reaction medium which is inert to the reaction may be employed. Suitable reaction media include N,N-dimethylformamide and dioxane.

The reaction of this invention may be conducted either at atmospheric pressure, under a pressure above atmospheric pressure or under a reduced pressure.

The reaction of this invention may be conducted either batchwise or continuously.

According to this invention, carboxylic acid amides can be obtained from aldehydes and ammonia or primary amines or secondary amines at high yields in one step under mild reaction conditions and thus, the process of this invention is very advantageous from an economic viewpoint.

The following examples are given to illustrate the present invention more specifically. However, it should be understood that the invention is in no way limited by these examples.

EXAMPLE 1

In a 100 ml three-necked flask were charged 2 g of pyridine-3-aldehyde, 50 g of a 28 weight percent aqueous ammonia solution and 2 g of a commercially available palladium catalyst in which 5 percent by weight of palladium metal had been supported on carbon (product of Engelhard Co., Ltd.), and the reaction was conducted at a reaction temperature of 40° C. for 2 hours by introducing oxygen at a rate of 10 l/hour into the flask from its gas inlet equipped with a filter.

After the reaction the reaction mixture solution was subjected to gas chromatography. As a result, the conversion of pyridine-3-aldehyde was 67% and the yield of nicotinic acid amide was 57%.

EXAMPLE 2

In the same flask as in Example 1 were charged 2 g of benzaldehyde, 60 g of dioxane as the reaction medium and 3 g of the same commercially available palladium catalyst as in Example 1 and the inner temperature of the flask was maintained at 50° C. The reaction was conducted by introducing ammonia gas at a rate of 1 l/hour and air at a rate of 10 l/hour into the flask at the same time for 3 hours to given benzamide at a yield of 49% based on the feed benzaldehyde.

EXAMPLE 3

In the same flask as in Example 1 were charged 2 g of pyridine-3-aldehyde, 60 g of a 40 weight percent aqueous dimethylamine solution and 2 g of a commercially available palladium in which 5 percent by weight of palladium metal had been supported on alumina (product of Engelhard Co., Ltd.), and the reaction was conducted at a reaction temperature of 50° C. by introducing oxygen at a rate of 5 l/hour into the flask for 3 hours to give the following results.

Conversion of pyridine-3-aldehyde: 79%.
Yield of nicotinic acid dimethylamide: 62%.

EXAMPLE 4

In the same apparatus as in Example 1 were charged 2 g of tetraoxane as a source for formaldehyde, 60 g of a 40 weight percent aqueous dimethylamine solution and 3 g of the same commercially available palladium as in Example 3, and the reaction was conducted at a reaction temperature of 40° C. by introducing oxygen at a rate of 6 l/hour for 3 hours to give N,N-dimethylformamide at a yield of 61%.

EXAMPLE 5

In a 100 ml three-necked flask were charged 2 g of pyridine-3-aldehyde, 50 g of a 28 weight percent aqueous ammonia solution and 3 g of a catalyst in which 5 percent by weight of palladium metal together with lead oxide with an atomic ratio of Pd to Pb being 1 to 3 had been supported on active carbon. The reaction was conducted in the same manner as in Example 1 to give the following results.

Conversion of pyridine-3-aldehyde: 81%.
Yield of nicotinic acid amide: 77%.

EXAMPLE 6

In the same flask as in Example 1 were charged 2 g of benzaldehyde, 50 g of dioxane as the reaction medium and 2 g of a catalyst in which 5 percent by weight of palladium metal together with thallium nitrate with an atomic ratio of Pd to Tl being 1 to 0.1. The reaction was conducted at a reaction temperature of 40° C. by introducing ammonia gas at a rate of 1 l/hour and oxygen at a rate of 10 l/hour at the same time into the flask for 2 hours to give benzamide at a yield of 71%.

EXAMPLE 7

In the same flask as in Example 1 were charged 2 g of furfural, 60 g of dioxane as the reaction medium and 2 g of the same commercially available palladium catalyst as in Example 1 and the inner temperature of the flask was maintained at 50° C. The reaction was conducted by introducing ammonia gas at a rate of 1 l/hour and oxygen at a rate of 10 l/hour at the same time into the flask for 2 hours to give furfurylamide at a yield of 51% based on the feed furfural.

EXAMPLE 8

In the same flask as in Example 1 were charged 2 g of pyridine-3-aldehyde, 60 g of a 40 weight percent aqueous dimethylamine solution and 2 g of a catalyst in which 4 percent by weight of palladium metal together with mercuric chloride with an atomic ratio of Pd to Hg being 1 to 0.1 had been supported on active carbon. The reaction was conducted at a reaction temperature of 40° C. by introducing oxygen at a rate of 6 l/hour into the flask for 2 hours to give the following results.

Conversion of pyridine-3-aldehyde: 81%.
Yield of nicotinic acid dimethylamide: 75%.

EXAMPLE 9

In a 100 ml three-necked flask were charged 2 g of pyridine-3-aldehyde, 30 g of a 28 weight percent aqueous ammonia solution and 5 g of a catalyst in which 3 percent by weight of palladium metal together with lead metal and lead oxide with an atomic ratio of Pd to Pb being 1 to 2 and a weight ratio of Pb to PbO being 1 to 2 had been supported on alumina. The reaction was conducted in the same manner as in Example 1 and the results were as follows:

Conversion of pyridine-3-aldehyde: 77%.
Yield of nicotinic acid amide: 74%.

EXAMPLE 10

In the same flask as in Example 1 were charged 2 g of methacrolein, 20 g of a 40 weight percent aqueous dimethylamine solution, 30 g of dioxane as the reaction medium and 3 g of a commercially available platinum catalyst in which 5 percent by weight of platinum metal had been supported on active carbon and the inner temperature of the flask was maintained at 30° C. The reaction was conducted by introducing oxygen at a rate of 4 l/hour into the flask for one hour to give methacryl dimethylamide at a yield of 19% based on the feed methacrolein.

EXAMPLE 11

In the same flask as in Example 1 were charged 2 g of pyridine-3-aldehyde, 5 g of benzylamine, 40 g of N,N-dimethylformamide and 3 g of a catalyst in which 5 percent by weight of platinum metal together with lead hydroxide with an atomic ratio of Pt to Pb being 1 to 1 had been supported on alumina. The reaction was conducted at a reaction temperature of 25° C. by introducing air into the flask at a rate of 6 l/hour for 2 hours to give nicotinic acid benzylamide at a yield of 23%.

EXAMPLE 12

In a 100 ml three-necked flask were charged 2 g of pyridine-3-aldehyde, 50 g of a 30 weight percent aqueous ethylamine solution and 3 g of the same commercially available palladium catalyst as in Example 1. The reaction was conducted at a reaction temperature of 30° C. for 2 hours by introducing oxygen at a rate of 10 l/hour into the flask from its gas inlet equipped with a filter to give nicotinic acid monoethylamide at a yield of 47%.

EXAMPLE 13

In a 100 ml three-necked flask were charged 2 g of benzyl 7-aminocephalosporanate, 10 g of benzaldehyde, 50 g of N,N-dimethylformamide as the reaction medium and 3 g of a platinum catalyst in which 5 percent by weight of platinum metal had been supported on silica and the inner temperature of the flask was maintained at 25° C. The reaction was conducted by introducing oxygen at a rate of 5 l/hour into the flask from its gas inlet for 2 hours with sufficient agitation to give benzyl 7-N-benzoylcephalosporanate at a yield of 12% based on the feed benzyl 7-aminocephalosporanate.

While the invention has been described in detail and with reference to specific embodiments thereof, it will be apparent to one skilled in the art that various changes and modifications can be made therein without departing from the spirit and scope thereof.

What is claimed is:

1. A process of preparing a carboxylic acid amide which comprises reacting (a) an aldehyde selected from the group consisting of formaldehyde; acetaldehyde; propionaldehyde; pivalinaldehyde; caprylaldehyde; acrolein; methacrolein; benzaldehyde; tolualdehyde; cinnamaldehyde; furfural; pyridinealdehyde; thiophenealdehyde; pyrrolealdehyde; benzaldehyde, tolualdehyde and cinnamaldehyde whose aromatic ring is substituted with a halogen atom, an alkyl group having 1 to 5 carbon atoms, a haloalkyl group having 1 to 5 carbon atoms or an alkoxy group; furfural, pyridinealdehyde, thiophenealdehyde and pyrrolealdehyde whose heterocyclic ring is substituted with an alkyl group having 1 to 5 carbon atoms or a haloalkyl group having 1 to 5 carbon atoms; glyoxal and glutardialdehyde, with (b) at least one compound selected from the group consisting of ammonia, methylamine, ethylamine, propylamine, isopropylamine, butylamine, cyclopentylamine, cyclohexylamine, aniline, toluidine, naphthylamine, benzylamine, xylidenediamine, primary amines having a penicillin skeleton or a cephalosporin skeleton, dimethylamine, diethylamine, di-n-propylamine, methylethylamine, methylaniline, ethylaniline, piperidine, piperazine, pyrazoline, pyrrolidine, pyroline, and primary and secondary amines having as a substituent a halogen atom, an alkyl group or an alkoxy group, by introducing a molecular oxygen- containing gas in the presence of a catalytic amount of palladium metal or platinum metal at a reaction temperature of from about 0° C. to about 200° C.

2. The process of claim 1, wherein (a) is selected from the group consisting of formaldehyde, acrolein and methacrolein and (b) is selected from the group consisting of ammonia, methylamine, ethylamine, dimethylamine, diethylamine and methylethylamine.

3. The process of claim 1, wherein the amount of the compound (b) ranges from about 0.002 mole to about 100 moles per mole of the aldehyde (a).

4. The process of claim 1, wherein the palladium metal or platinum metal is present to the extent of about 0.1 to about 20 percent by weight on a carrier selected from the group consisting of active carbon, silica and alumina.

5. The process of claim 1, wherein along with the palladium metal or the platinum metal there is incorporated at least one metal atom selected from lead, thallium and mercury, the metal atom being present as the metal per se, the inorganic acid salt, the organic acid salt, the oxide or the hydroxide, and the atomic ratio of lead, thallium or mercury to palladium or platinum ranges from about 0.01 to 30.

6. The process of claim 1, wherein the molecular oxygen is used at least in a stoichiometric amount required for the reaction.

7. The process of claim 1, wherein the reaction is carried out in an inert reaction medium.

8. The process of claim 7, wherein the inert reaction medium is N, N-dimethylformamide or dioxane.

9. The process of claim 1, wherein the reaction temperature ranges from about 15° C. to about 150° C.

10. The process of claim 2, wherein the amount of the compound (b) ranges from about 0.002 mole to about 100 moles per mole of the aldehyde (a), the palladium metal or platinum metal is present to the extent of about 0.1 to about 20 percent by weight on a carrier selected from the group consisting of active carbon, silica and alumina, along with the palladium metal or the platinum metal there is incorporated at least one metal atom selected from lead, thallium and mercury, the metal atom being present as the metal per se, the inorganic acid salt, the organic acid salt, the oxide or the hydroxide, and the atomic ratio of lead, thallium or mercury to palladium or platinum ranges from about 0.01 to 30, the molecular oxygen is used at least in a stoichiometric amount required for the reaction, and the reaction is carried out at about 15° to 150° C. in N, N-dimethylformamide or dioxane.

* * * * *